United States Patent [19]

Bullard et al.

[11] Patent Number: 5,003,963
[45] Date of Patent: Apr. 2, 1991

[54] LARYNGOSCOPE

[75] Inventors: James R. Bullard, 707 Somerset Way, Augusta, Ga. 30909; Richard P. Muller, Bronx, N.Y.; Benedetto Grossi, Stamford, Conn.; John Cristine, Bath, N.Y.

[73] Assignee: James Roger Bullard, Augusta, Ga.

[21] Appl. No.: 489,272

[22] Filed: Mar. 5, 1990

Related U.S. Application Data

[60] Division of Ser. No. 315,214, Feb. 23, 1989, Pat. No. 4,905,669, which is a continuation of Ser. No. 101,834, Sep. 28, 1987, abandoned.

[51] Int. Cl.⁵ .............................................. A61B 1/26
[52] U.S. Cl. .................................. 128/11; 128/200.26
[58] Field of Search ................... 128/4, 6, 10, 11, 207, 128/14, 15, 207.15, 200.24, 200.26; 606/106; 604/165

[56] References Cited

U.S. PATENT DOCUMENTS

| Re. 32,306 | 12/1986 | Waters | 604/165 |
|---|---|---|---|
| 1,246,338 | 11/1917 | Smit . | |
| 1,613,373 | 1/1927 | Beck . | |
| 1,638,986 | 8/1927 | DeZeng | 128/11 |
| 2,354,471 | 7/1944 | Macintosh | 128/10 |
| 2,765,785 | 10/1956 | Pagoto | 128/15 |
| 3,195,536 | 7/1965 | Hovnanian et al. | 128/6 |
| 3,598,113 | 8/1971 | Moore | 128/11 |
| 3,643,654 | 2/1972 | Felbarg | 128/11 |
| 3,677,262 | 7/1972 | Zukowski | 128/6 |
| 3,727,605 | 4/1973 | Klein | 128/11 |
| 3,766,909 | 10/1973 | Ozbey | 128/11 |
| 3,771,514 | 11/1973 | Huffman et al. | 128/11 |
| 3,776,222 | 12/1973 | Smiddy | 128/6 |
| 3,830,225 | 8/1974 | Shinnick | 128/4 |
| 3,863,627 | 2/1975 | Bouffard | 128/10 |
| 3,884,222 | 5/1975 | Moore | 128/11 |
| 3,913,568 | 10/1975 | Carpenter | 128/11 |
| 4,063,561 | 12/1977 | McKenna | 128/207.15 |
| 4,086,919 | 5/1978 | Bullard | 128/11 |
| 4,122,856 | 10/1978 | Mosior et al. . | |
| 4,329,983 | 5/1982 | Fletcher | 128/207.15 |
| 4,337,761 | 7/1982 | Upsher | 128/11 |
| 4,527,553 | 7/1985 | Upsher | 128/11 |
| 4,694,826 | 9/1987 | Chester | 128/20 |
| 4,832,020 | 5/1989 | Augusthe | 128/10 |
| 4,905,669 | 3/1990 | Bullard et al. | 128/11 |

FOREIGN PATENT DOCUMENTS

| 1251875 | 8/1986 | U.S.S.R. | 128/4 |
|---|---|---|---|
| 2133694 | 8/1984 | United Kingdom . | |

OTHER PUBLICATIONS

"Multi-Purpose Anterior Commissure Laryngoscopes", American V. Mueller p. 776.
"Fiberscope Cleaning and Disinfection" Advertisement, 1986, available in 128/11 USPTO.
Dec. 16, 1986 Official Gazette, p. 1156 Re 32,306.
Reichert Price List, Jul. 1, 1984.
"Design Breakthrough in Laryngoscopy" by J. Roger Bullard M.D., Oct. 1985.

*Primary Examiner*—Edward M. Coven
*Assistant Examiner*—Mark S. Graham
*Attorney, Agent, or Firm*—Perman & Green

[57] ABSTRACT

A method for moving an object in the larynx and trachea region of a patient for use with a laryngoscope having a working channel. A device device has an elongate shaft adapted for movement within the working channel of the laryngoscope. Located at a distal region of the shaft are grasping jaws. The placement device grasps an object, moves the object relative to the laryngoscope and releases the object from the placement device at a desired position.

6 Claims, 7 Drawing Sheets

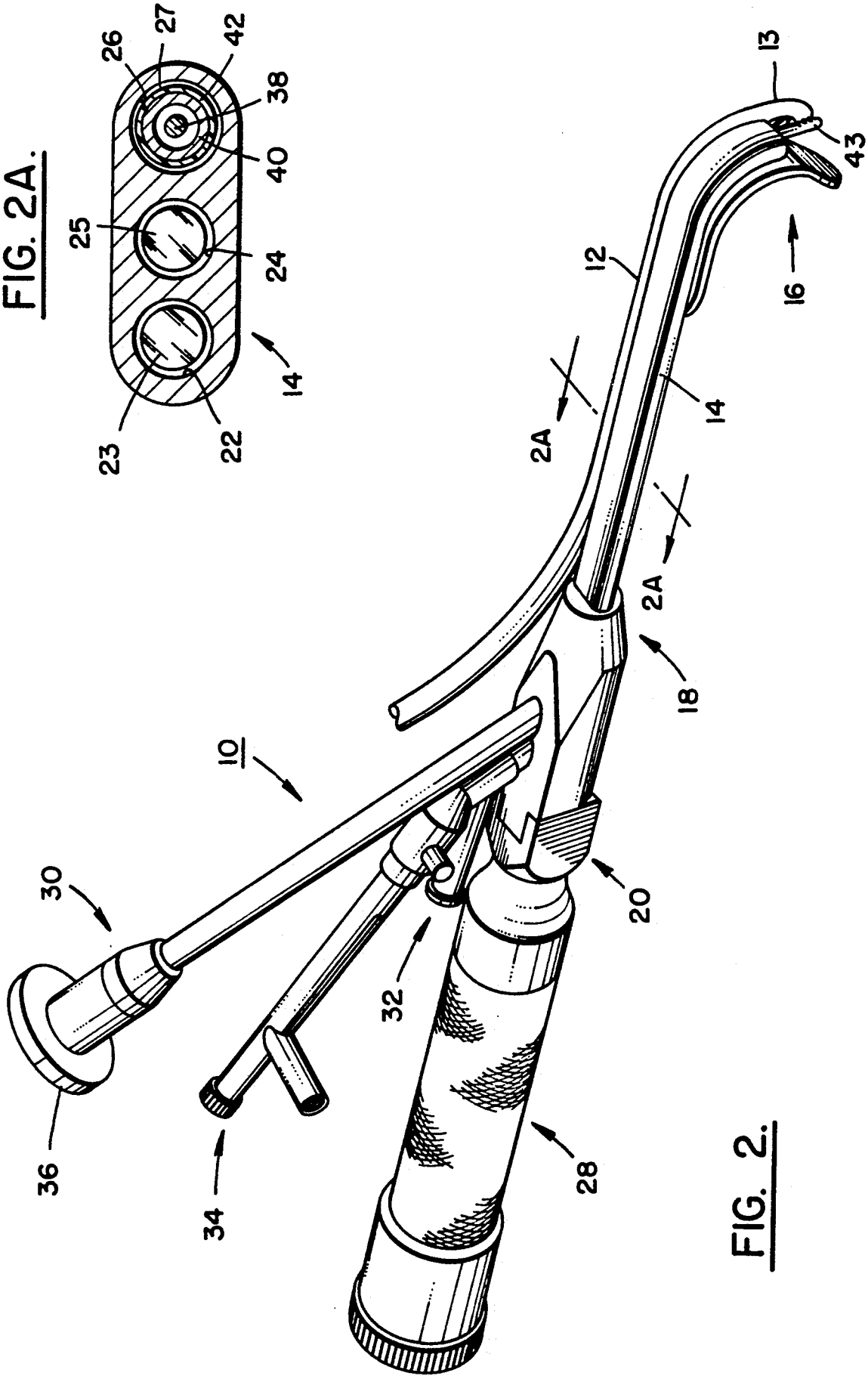

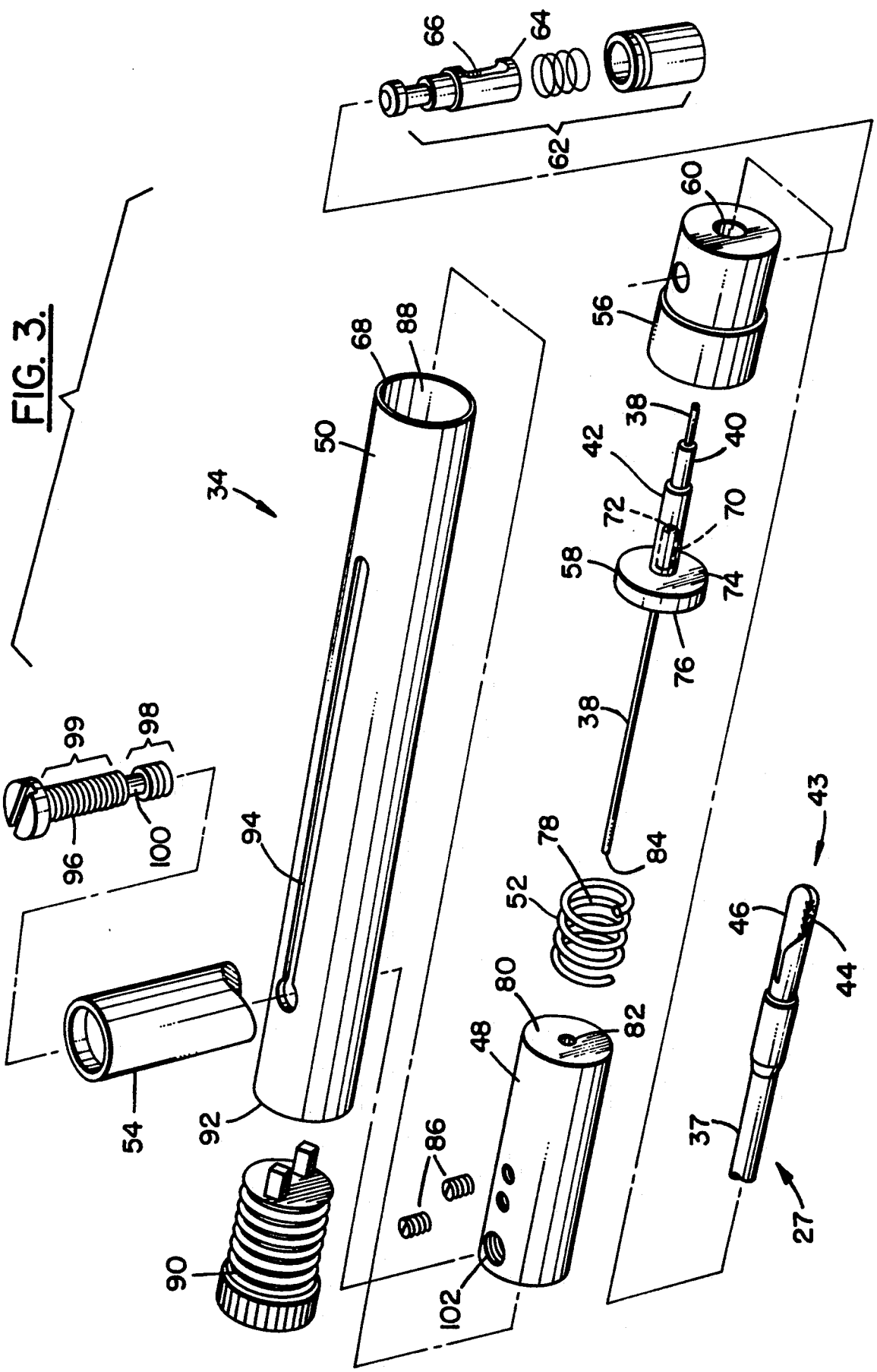

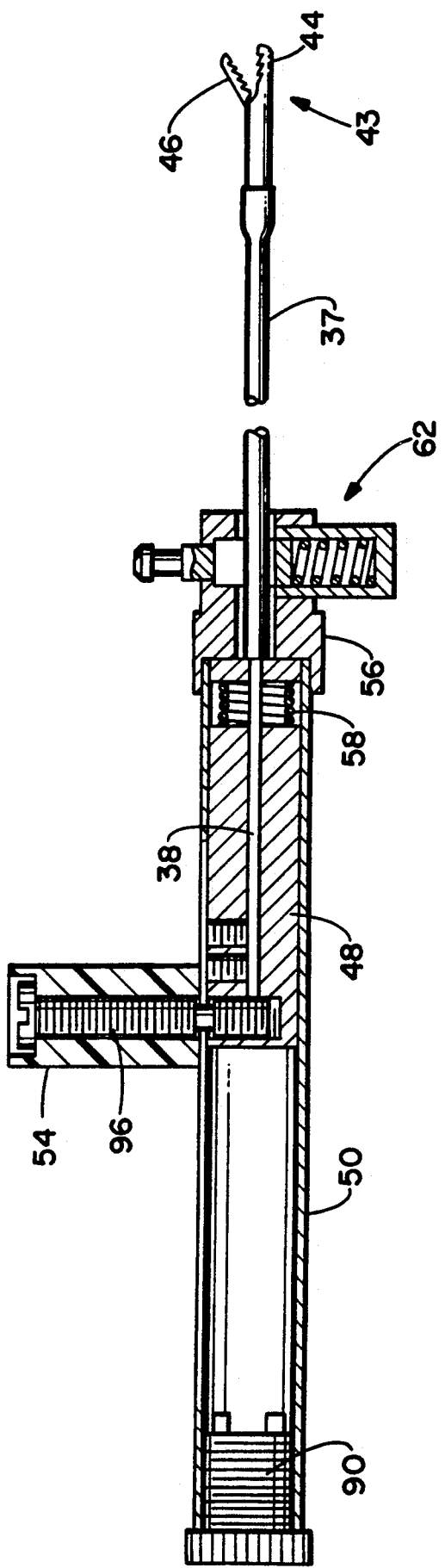

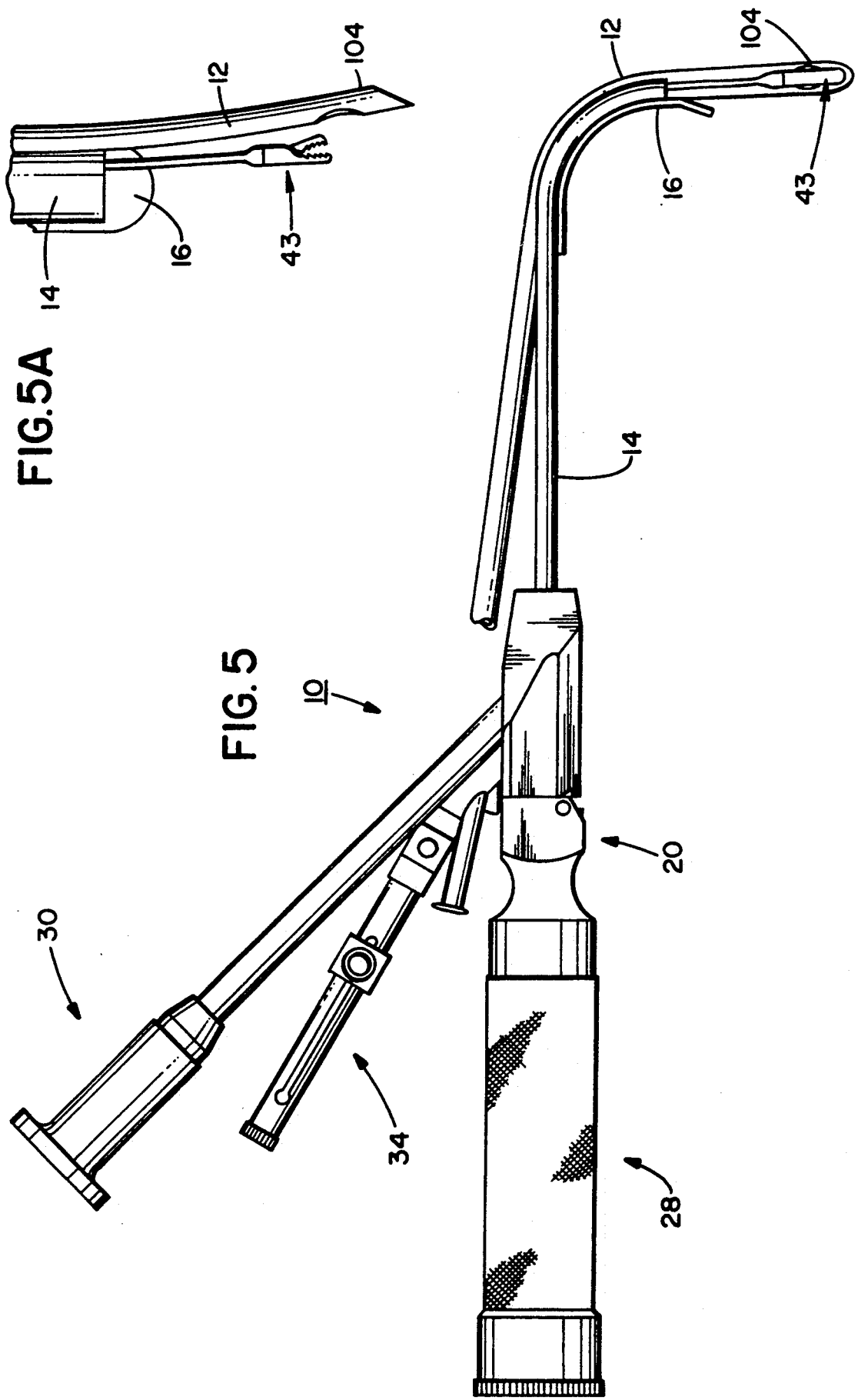

LARYNGOSCOPE

This is a divisional of copending application Ser. No. 07/315,214; filed Feb. 23, 1989, now U.S. Pat. No. 4,905,669, which is a continuation of Ser. No. 07/101,834; filed Sept. 28, 1987, now abandoned.

BACKGROUND OF THE INVENTION

1. Field of the Invention

The present invention relates to an instrument for accessing the laryngeal area of the human body and, more particularly, to an improved laryngoscope for use in intubation.

2. Prior Art

Laryngoscopes are widely known and used in the medical field to facilitate endotracheal intutation of a patient during surgery to provide a positive air passageway for the administration of anesthesia and/or for the mechanical ventilation of the lungs of the patient. In the human anatomy, the epiglottis normally overlies the glottis opening into the larynx to prevent the passage of food into the trachea during eating; therefore, in endotracheal intubation, it is necessary to displace the epiglottis from the glottal opening to permit the air tube to be inserted into the trachea.

Various laryngoscope constructions are known. The more widely used laryngoscopes consist of an elongate, rigid metal blade which is supportably attached to a handle and is inserted through the mouth of the patient into the pharyngeal area to displace the tongue and epiglottis and permit direct visualization of the glottis through the mouth opening. Such laryngoscopes are generally provided with a light source which is directed along the blade to illuminate the area beyond the distal end of the blade. Two general types of rigid blade constructions are the straight, or so called "Miller blade", and the slightly curved, or so called "MacIntosh blade." Curved laryngoscope blade constructions having light means to facilitate illumination of the areas of observation are described in U.S. Pat. Nos. 3,598,113; 3,643,654; 3,766,909; and 3,771,514.

The standard method for performing intubation of the trachea during surgery with rigid laryngoscope blades of the straight or slightly curved type is to place the patient in supine position, tilt the head backwards as far as possible, and distend the lower jaw to widely open the mouth. The rigid blade is then inserted through the mouth into the throat passageway to displace the tongue and epiglottis and expose the glottis of the patient. The larynx is then viewed through the mouth opening from an observation position just above and behind the head of the patient by sighting generally along the axis of the blade. The endotracheal tube is inserted, either orally or transnasally, and passed alongside the blade through the glottis.

Surgical instruments having means for indirect illumination and visualization of the pharyngeal areas of the body are known. U.S. Pat. Nos. 3,776,222 and 3,913,568 disclose devices for endotracheal intubation which comprise flexible or articulatable tubular probes having internal fiber optics for lighting and viewing the internal areas of the body. As disclosed in said patents, the probes carry a slidably removable endotracheal tube surrounding their outer surfaces and the probe is directly inserted into the trachea to position the tube. Such devices obviously require the use of relatively large diameter endotracheal tubes in order to be carried on the tubular probe, and their use necessarily is limited to patients with sufficiently large airway passages to accommodate the combined size of the probe and endotracheal tube. Additionally, due to the flexible nature of the probes, it is difficult to manipulate the probe to displace the tongue and epiglottis to permit direct insertion of the tube into the trachea.

U.S. Pat. No. 3,677,262 discloses a surgical instrument employing internal fiber optics in a rigid tube which carries an endotracheal tube surrounding its outer surface. The instrument not only requires the use of large endotracheal tubes with the limitations mentioned above, but its generally straight configuration requires hyperextension of the head and neck during use, as with the Miller and MacIntosh rigid, blade-type constructions described above.

U.S. Pat. No. 4,086,919 discloses a laryngoscope having an improved blade construction which is anatomically shaped which may be utilized for intubation of the trachea without disturbing the normal position of the head of a patient in supine position and without contacting the bony structure during use.

A problem arises; however, in the prior art in that it is relatively difficult to precisely place objects in the larynx and trachea regions of the patient.

A further problem arises in the prior art in that devices that merely push an endotracheal tube alongside a rigid blade do not have precise control of the leading portion of the tube. The result can be damage to the tissue of the patient during insertion and difficulty in precisely placing the tube.

A further problem arises in the prior art in that devices which slidably move endotracheal tubes around their outer surfaces are relatively large in cross-section size and may not be appropriate for all patients.

A further problem arises in the prior art in that devices which use internal fiber-optics for viewing areas in the patient and which slide intubation tubes around the outside circumference of the devices almost immediately obscure the operator's view.

A further problem arises in the prior art in that no special provision is made in using the devices for patients with individual health problems or for patients such as children which may require precise placement of an object or require a precise size tube for intubation.

SUMMARY OF THE INVENTION

The foregoing problems are overcome and other advantages are provided by a placement device and method for placing a workpiece in the larynx and trachea region of a patient.

In accordance with one embodiment of the invention, the placement device is adapted for use with a laryngoscope having a working channel. The placement device comprises an elongate shaft adapted for movement within the working channel of the laryngoscope. A grasping means is located at a distal region of the shaft. The grasping means is adapted to grasp, hold and release at least a portion of a workpiece such that the workpiece can be grasped, moved relative to the laryngoscope and released from the placement device at a desired position.

In accordance with an alternate embodiment of the invention, a laryngoscope is provided for use in the positioning of a tube into the larynx and trachea region of a patient. The laryngoscope comprises a rigid elongate blade having a proximal region, a distal region and a working channel. Located at the distal region is a means for positioning a leading portion of the tube from a first position proximate the blade distal region to a second position extended from the blade distal region. The positioning means has a movable extension means movably positioned with the working channel such that the positioning means can move the leading portion of a tube into the larynx and trachea region of a patient by moving the extension means.

In accordance with one method of the invention, an object can be placed into the larynx and trachea region of a patient. A laryngoscope is inserted into patient. The laryngoscope has a placement device movably connected therewith. The placement device has the object connected thereto. A distal portion of the placement device is moved from a first home position proximate a distal region of the laryngoscope to a second extended position. The object is also moved relative with the distal portion of the placement device. The object is then released from the placement device.

In accordance with another method of the invention, a tube can be placed in the larynx and trachea region of a patient. A leading portion of the tube is grasped by a grasping device located at a distal region of a relatively flexible placement device. The placement device is movably located within a working channel of the laryngoscope. The laryngoscope is inserted into the patient with the leading portion of the tube being located at a first position proximate the distal region of the laryngoscope. The placement device is moved to thereby extend the grasping device and the leading position of the tube to a second position. The tube is then released from the grasping device.

BRIEF DESCRIPTION OF THE DRAWINGS

The foregoing aspects and other features of the invention are explained in the following description, taken in connection with the accompanying drawings wherein:

FIG. 2 is a perspective view of a laryngoscope having features of the invention.

FIG. 2a is a cross-sectional view of the blade of the laryngoscope in FIG. 2 taken along line 2a—2a.

FIG. 3 is an exploded view of the grasping and extending device and control of the instrument shown in FIG. 2.

FIG. 4c is a diagrammatical cross-sectional view of the control of FIG. 4b at an extending and releasing position.

FIG. 5 is a side view of the instrument in FIG. 2 with the grasping and extending device and control at the second position.

FIG. 5a is a top view of the distal region of the instrument in FIG. 5 with the intubation tube released.

DETAILED DESCRIPTION OF THE INVENTION

Figure 1:
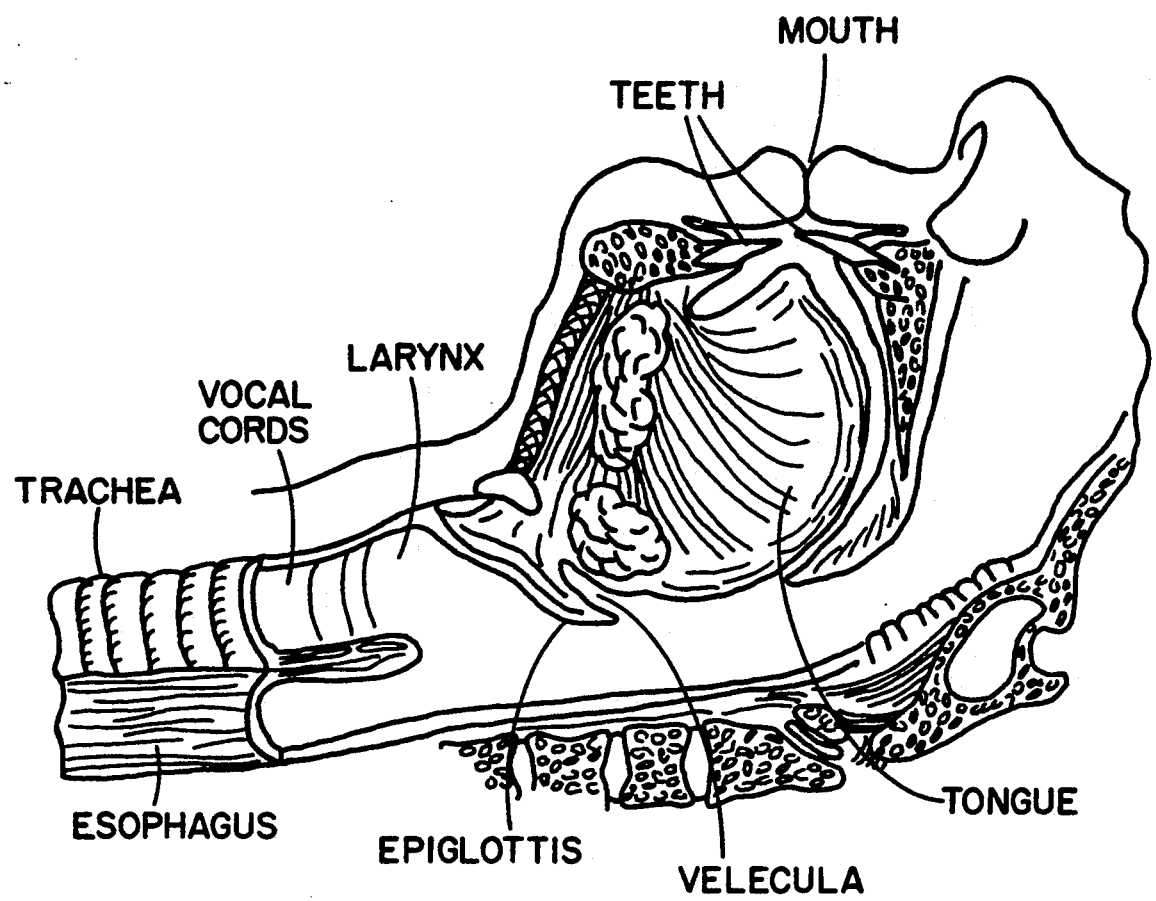
FIG. 1 is a diagrammatical cross-sectional side view of a human lower head and neck region.

Referring to FIG. 1, there is shown a diagrammatical cross-sectional side view of a human lower head and neck region. As shown in the figure, cavities or passageways from the mouth and nose combine to communicate with the esophagus and trachea. The epiglottis can cover the opening to the trachea during ingestion of food or liquids. As apparent from the figure, there is no normal straight path from the cavities of the mouth and nose to the larynx and trachea because of the anatomical shape of the human body.

Referring now to FIG. 2, there is shown a perspective view of one embodiment of the invention. In this embodiment, a laryngoscope 10 is intended for use for inserting an intubation or endotracheal tube 12 into the trachea of a patient. The laryngoscope 10 has a relatively rigid blade 14 of an anatomically curved configuration and made of a suitable material such as metal or plastic. The blade 14 has a distal end 16 intended for leading insertion into the patient's mouth and a proximal end 18 connected to a control head 20.

Figure 9:
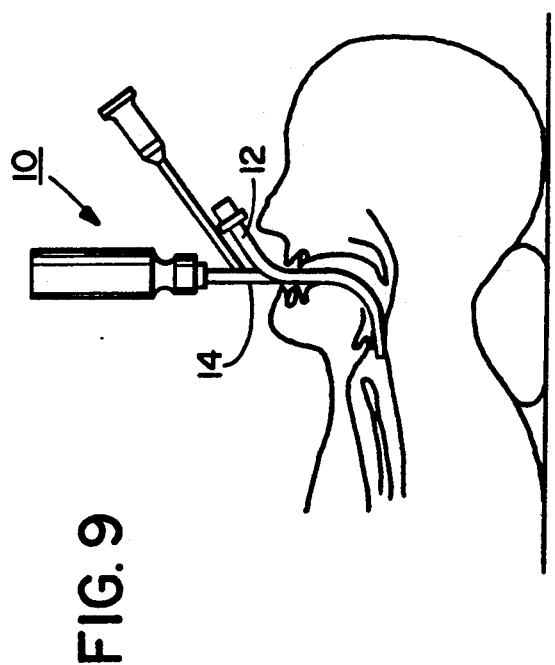
FIG. 9 is an illustrative view of a laryngoscope having a curved blade inserted into a patient.

The exterior configuration of the blade 14 is similar to the instrument disclosed in U.S. Pat. No. 4,086,919 by the same inventor as herein which is incorporated by reference in its entirety herein. As shown in FIG. 9, with the patient in supine position the blade 14 can be inserted into the mouth of the patient. In the event the epiglottis is enlarged or otherwise malformed in such a way that it is not readily displaced from the glottis with the tip inserted into the velecula, the tip or distal end 16 may just as readily be placed directly beneath the epiglottis itself and the blade raised vertically to expose the glottis. The device shown in FIG. 2 is generally for use with various sizes and types of intubation tubes such as cuffed or uncuffed or having an inner diameter of from about 2.5 mm to about 10 mm. However, as will become apparent virtually any size, shape or type of intubation tube can be inserted into a patient by this embodiment.

Referring also to FIG. 2a there is shown a cross-sectional view of the blade 14 of FIG. 2 taken along line 2a—2a. As shown in this embodiment, the blade 14 comprises three relatively continuous channels; an illumination channel 22, an image channel 24 and a working channel 26. Although there are three channels shown in relatively linear arrangement in this embodiment, any number of channels may be used and the channels may be arranged in any suitable type of configuration. The illumination channel 24 in this embodiment is provided to house a bundle 23 of light transmitting fibers. The bundle 23 is connected to a suitable light source (not shown) and transmits light to the distal end 16 of the blade 14 where it can illuminate a target area or pathway. The image channel 24 is provided to house a second bundle 25 of image transmitting fibers. The second bundle 25 is connected to a suitable image viewing device 30 and transmits images of the areas proximate the distal end 16 to the image viewing device 30 for observation. However, as will become apparent, any type of means could be used to illuminate or visualize a target area.

The working channel 26 is provided for housing a grasping and extending device or an intubation tube installation device 27. The working channel 26 communicates from the control head 20 to an opening at the distal end 16 of the blade 14. The grasping and extending device 27, in the embodiment shown, is generally intended for grasping and holding a leading portion of a intubation tube during insertion of the laryngoscope 10 into a patient, controllably extending the tube into a desired position and then releasing the tube from the device 27. The grasping and extending device shown generally comprises a grasping means 43, an elongate flexible shaft 37 and a control 34 which will be described in further detail below. As shown in FIG. 2, the grasping means 43 is connected to the tube 12 at the tube leading edge 13 with the tube being positioned along the side of the blade 14.

In the embodiment shown in FIG. 2, the control head 20 comprises four main sections; a handle/power section 28, an image viewing device 30, a working channel secondary entry 32 and a grasping and extension control 34. The handle/power section 28, in this embodiment, is provided for the operator to securely hold the laryngoscope 10 and control its insertion into and removal from the patient. The handle/power section 28 also has an interior cavity (not shown) for retaining a power source such as dry cell batteries (not shown). The batteries (not shown) communicate with a light source (not shown) in the control head 20 which provides light to the fiber-optic illumination bundle 23 to illuminate the area adjacent the blade distal end 16. However, any suitable light source configuration can be used. The handle/power section 28, in this embodiment, is also disconnectable from the control head 20 for such occasions as cleaning or storage of the instrument 10.

The image viewing device 30, in this embodiment, comprises an eyepiece 36, optical lens (not shown) and at least a portion of the image bundle 25. Thus, the operator can view the area proximate the distal end 16 of the blade 14 by viewing the image at the eyepiece 36 carried by the image bundle 25. However, any suitable image viewing device can be used such as a television camera. The working channel secondary entry 32 communicates with the working channel 26 of the blade 14 and can be used for such tasks as cleaning the working channel 26, transmitting gases to the pharyngeal area or allowing the removal of liquids such as secretions or blood by suction. The grasping and extending device 27 can be removed from the instrument 10 for these purposes.

Referring now to FIGS. 2a and 3, FIG. 3 shows an exploded view of the grasping and extending device 27 and control 34 of the instrument in FIG. 2. The grasping and extension device 27, in the embodiment, comprises a shaft 37 having a connecting member 38, a sheath 40 and a protective cover 42. The connecting member 38 can generally be a compressively stable wire. The wire 38 is generally surrounded by the sheath 40 which increases stability to the shaft 37, but also allows for shaft flexibility and movement of the wire 38 in the sheath 40.

The protective cover 42 can be made of any suitable material which allows easy cleaning of the shaft and provides a smooth surface for easy movement of the shaft 37 in the working channel 26.

Located at the distal end of the grasping and extension device 27 is a grasping means 43 comprising a set of single action jaws 44 and 46 for grasping a leading portion of the tube (not shown). A first jaw 44 is relatively stationary with respect to device 27 and is fixed with the sheath 40. A second jaw 46 is pivotally pinned with the device 27 and has the connecting member 38 connected thereto such that movement of the connecting member 38 relative to the sheath 40 will cause the second jaw 46 to pivot to open and close the jaws. The jaws are generally smooth in profile to prevent damage to tissue during extension and retraction in the patient.

The control 34, in this embodiment, generally controls at least two functions of the grasping and extension device 27. First, the control 34 can control the movement of device 27 in the working channel 26 of the blade 14. Second, the control 34 can control the operation of the grasping means 43 at the distal end of the device 27. In the embodiment shown in FIG. 3 the control 34 can control the movement of the second jaw 46.

The control 34 shown in FIG. 3 generally comprises a relatively stationary contact sleeve or hub 56, a shaft stop sleeve or flange 58, a grasping biasing spring 52, a push block 48, a stationary slide tube 50 and a control lever 54. The contact sleeve 56 has a central aperture 60 being sized to accommodate the shaft 37 and allow movement therethrough. The sleeve 56 has a keying lock 62 for stationary yet removable positioning of the control 34 on the control head 20. The lock 62 has a detent 64 with a central aperture 66 for passage of the shaft 37 in both its compressed and extended positions. The sleeve 56 can be mounted to a first end 68 of the slide tube 50 and has an interior face (not shown) for contacting the stop sleeve 58.

The stop sleeve 58 generally has a sheath mounting ledge 70 and a central aperture 72. The sheath 40 and cover 42 of the shaft 37 terminate at the stop sleeve 58 and are mounted to the ledge 70. The central aperture 72 is sized to accommodate the connecting member 38 and allow for movement therethrough. Thus, if the stop sleeve 58 is retained in a stationary position the sheath 40 and cover 42 are retained in a relatively stationary position. However, the connecting member 38 is nonetheless capable of movement through the central aperture 72 of the stop sleeve 58 and shaft 40 to move the jaw 46 at the distal end of the graspsing and extending device 27. The stop sleeve 58 is sized to allow relatively free movement of the sleeve in the slide tube 50. The stop sleeve 58 also has a first face 74 for contracting the contact sleeve 56 and a second face 76 for contacting the biasing spring 52.

The biasing spring 52, in this embodiment, is provided to bias the second jaw 46 in a closed position. The spring 52 has a central passageway 78 which accommodates the connecting member 38 and is positioned between the second face 76 of the stop sleeve 58 and a first face 80 of the push block 48. The spring 52 is generally sized and shaped to be capable of movement in the slide tube 50. The push block 48 is also sized and shapd to move in the slide tube 50. The block 48 has a central aperture 82 which accommodates the connecting member 38. A proximal end 84 of the connecting member 38 is positioned in the central aperture 82 and fixedly attached to the block by locking screws 86. During assembly of the control 34 the biasing spring 52 is slightly compressed between the stop sleeve 58 and the push block 48 when the connecting member 38 is fixed to the push block 48 such that after assembly the biasing spring 52 will tend to force the stop sleeve 58 and block 48 apart. Since the connecting member 38 is fixed to the block 48 and the sheath 40 and cover 42 are attached to the stop sleeve 58 the biasing spring 52 causes the connecting member 38 to be pulled and the sheath 40 and cover 42 to be pushed such that the grasping means 43 at the distal end of device 27 will have the second jaw 46 automatically biased against the first jaw 44. The biasing spring 52 will be stopped from further expansion due to the two jaws 44 and 46 contacting one another.

The block 48, spring 52, stop sleeve 58 and proximal portion of the shaft 37 are positioned in an interior cavity 88 of the slide tube 50. The contact sleeve 56 is fixed to the first end 68 of the slide tube 50 and a second end stopper 90 is connected to a second end 92 of the slide tube 50. The contact sleeve 56 and stopper 90 act as barriers or limits to confine movement of the push block 48 in the interior cavity 88. The slide tube 50 also has a longitudinal guide slot 94 which communicates between the exterior of the slide tube 50 and the interior cavity 88. A screw 96 is provided with threaded areas 98 and 99 and a narrow portion 100 which is sized for movement in the guide slot 94. The screw 96 is positioned through an interior passageway of the control lever 54 through an enlarged area of the guide slot 94 and into a cooperating threaded hole 102 in the push block 48. The first threaded portion 98 of the screw is screwed into the hole 102 and thereby attaches the control lever 54 to push block 48 while also positioning the narrow portion 100 for movement in the guide slot 94. In the embodiment shown, the screw 96 is tightened between the control lever 54 and push block 48 such that frictional forces between the lever 54 and slide tube 50 and the push block 48 and slide tube 50 can retain the interior assembly at a desired position with the friction only being overcome by the operator pushing or pulling the control lever 54. However, any suitable type of position retention device or system can be used. Although the grasping and extending device 27 and control 34 have been described in great detail in this embodiment, it is to be understood that various alternate embodiment can be used with the present invention.

Figure 4A:
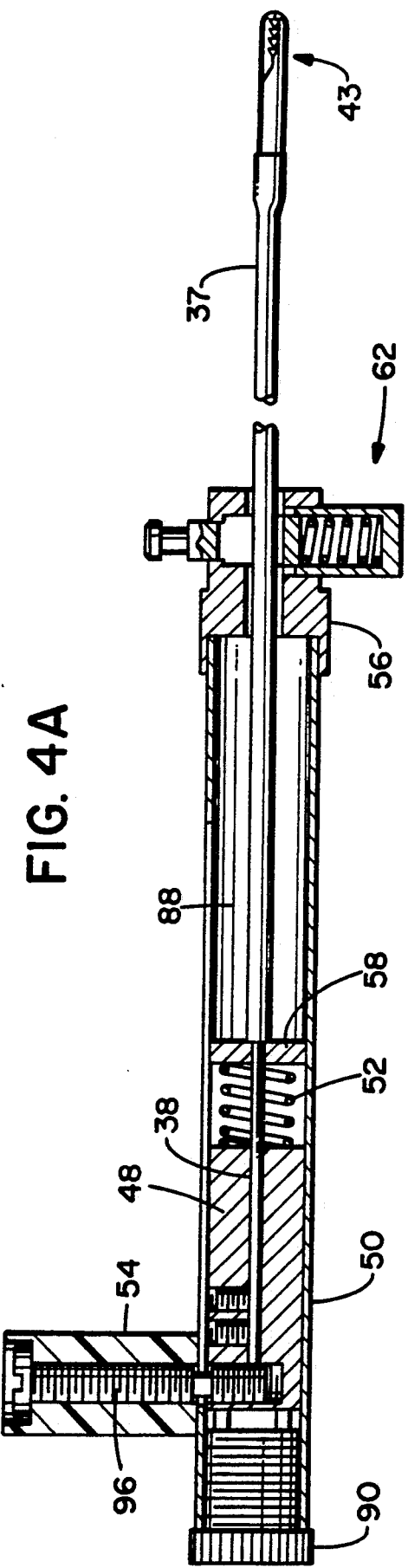
FIG. 4a is a diagrammatical cross-sectional view of the control in FIG. 3 at a first position.
Figure 4B:
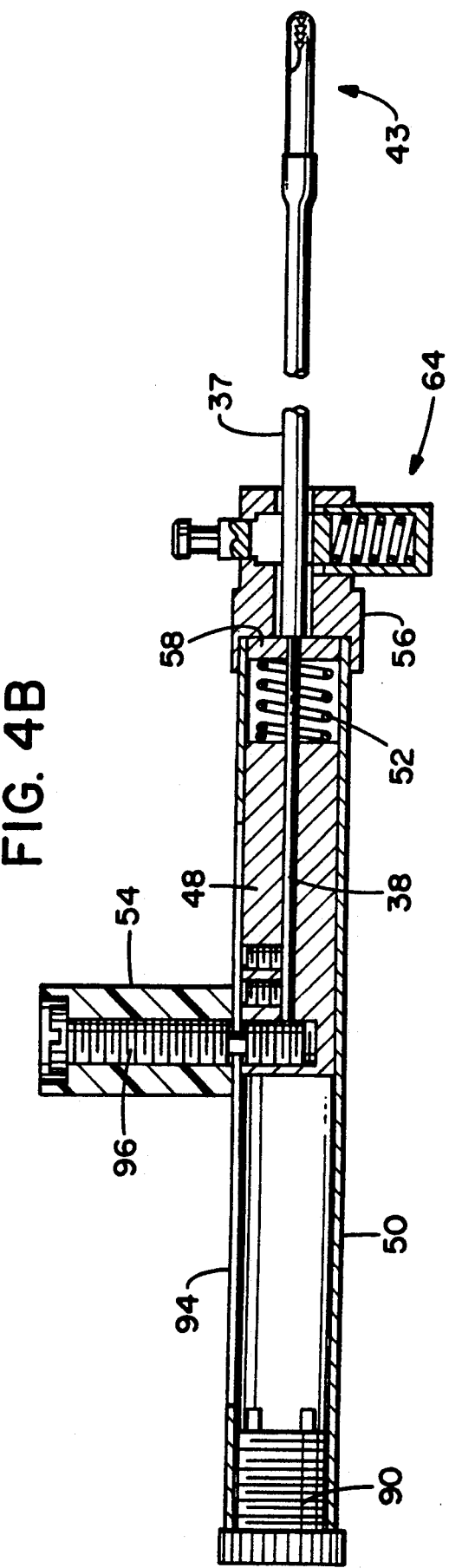
FIG. 4b is a diagrammatical cross-sectional view of the control of FIG. 4a at a second extended position.

Referring now to FIGS. 4a, 4b and 4c, diagrammatical cross-sectional views of the control 34 and grasping and extension device 27 are shown in three different positions. FIG. 4a shows a first or home position. The control lever 54 is in a fully retracted position with the push block 48 contacting the stopper 90. The poximal end 84 of the connecting member 38 and the proximal end of the sheath 40 and cover 42 are also in a retracted position with the biasing spring 52 being slightly compressed between the push block 48 and stop sleeve 58 such that the jaws 44 and 46 are biased in a closed position. With the control 34 and grasping and extending device 27 mounted with the laryngoscope as shown in FIG. 2, the lock 62 mounts the control onto the control head 20 with the shaft 37 passing through the control head into the working channel 26 in the blade 14 and the grasping means 43 being located proximate the distal end 16 of the blade 14.

The operetor, by pushing on the control lever 54, can move the push block 48, biasing spring 52, stop sleeve 58 and shaft 37 along the interior cavity 8 of the slide tube 50 to a second extended position as shown in FIG. 4b. The guide slot 94 and screw 96 cooperate to keep the control 34 and device 27 oriented in a relatively constant position. In the second position, the stop sleeve 58 contacts the contact sleeve 56. However, the biasing spring 52 has not been additionally compressed. Thus, the jaws 44 and 46 remain biased in a closed position as the control 34 moves between the first and second positions. As the control 34 has been moved, the entire grasping and extending device 27 has moved relative to the laryngoscope. The shaft 37 has longitudinally move along the working channel 26 of the blade 14. The grasping means 43 has also moved from a first position proximate the blade distal end 16 to a second position which is extended from the blade distal end 16 as illustrated is FIG. 5. In a preferred embodiment the second position is from about $\frac{3}{4}$ inch to about $1\frac{1}{2}$ inches from the first position. However, any desired amount of travel can be accommodated.

Referring to FIG. 4c, the grasping and extending device 27 is shown in the second position with the jaws 44 and 46 open and the control 34 at a third jaws opening position. In the position shown, the distal end of the device 27 remains stationary relative to the laryngoscope at the second extended position. However, the operator, by pushing on the control lever 54, has moved the push block 48 relative to the stop sleeve 58 and compressed the spring 52. The connecting member 38 moves forwared with the sheath 40 and cover 42 remaining relatively stationary. The connecting member 38 pushes on the second jaw 46 which causes the jaw to move about the pivot thereby opening the jaw 46 relative to jaw 44. As illustrated in FIG. 5a, when the jaws 44 and 46 open, the intubation tube 12 can be released from the device 27.

Referring now to FIGS. 2, 5 and 5a, the use of this particular embodiment will be described in inserting an intubation tube into the trachea region of a patient. Before insertion of the laryngoscope 10 and tube 12 into the patient, the operator will extend the device 27 to the second extended position and open the jaws 44 and 46. The operator can then attach the intubation tube 12 to the device 27. In a preferred method of attaching the leading portion of a tube to the device 27, the jaws 44 and 46 grasp the tube proximate a Murphy eye 104 is the tube. However, any suitable grasping or connecting means could be used to attach or connect the tube 12 with the grasping and extending device 27.

Figure 6:
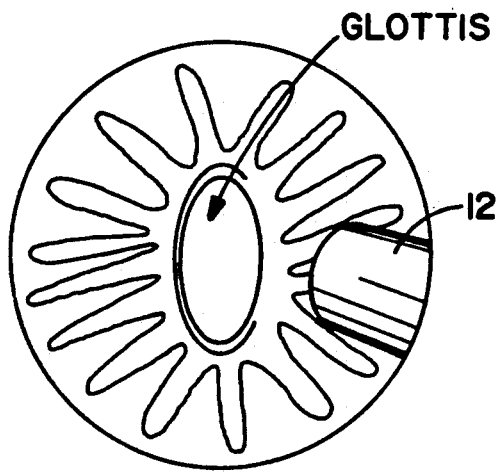
FIG. 6 is an illustrative view of what would be viewed by an operator of the instrument in FIG. 2 with the instrument inserted in a patient with the distal end of the instrument proximate the patient's glottis and the instrument in a home position.
Figure 7:
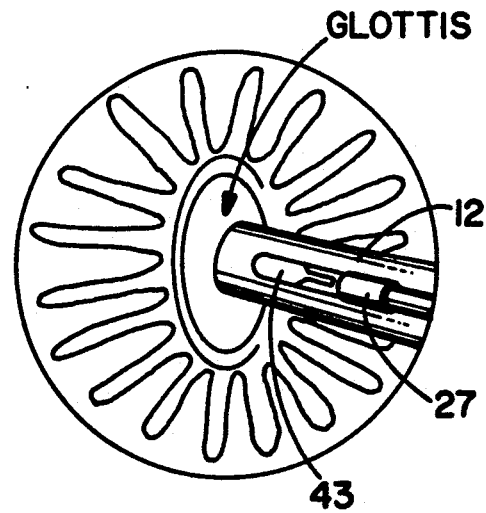
FIG. 7 is an illustrative view as in FIG. 6 with the instrument having the grasping and extending device being extended towards an extended second position.

After the tube 12 has been grasped, the device 27 is retracted to the first or home position illustrated in FIG. 2. The operator can then insert the blade 14 and tube 12 into the mouth and throat of the patient as diagrammatically illustrated in FIG. 9. Once the blade 14 has been fully inserted, the operator can view the target area, in this case the glottis or vocal cords, as illustrated in FIG. 6. The operator can now position the tube 12 through the glottis. As shown in FIG. 6, at the home position, the operator can view both the target area and a leading portion of the tube 12. The operator can move the control lever 54 forward thereby extending the device 27 towards the second extended position as illustrated in FIG. 5. The grasping and extending device 27 is urged through the working channel 26 of the blade 14 and advances the grasping means 43 and leading edge of the tube 12 towards the target area. Preferably, the vocal cords have been relaxed via a muscle relaxant to widen the opening. As illustrated in FIG. 7, the control head 20 and blade 14 of the laryngoscope remains stationary as the device 27, and tube 12 are urged forward and the operator's field of view remains relatively constant. The operator can, if necessary, move the laryngoscope to adjust the eventual positioning of the tube 12 or passage through the glottis.

Once the leading portion of the tube 12 has been properly positioned, the operator can release the tube 12 from the grasping means 43 as shown in FIG 5a. The second jaw 46 is capable of pivoting about 90 degrees to allow the tube 12 and grasping and extending device 27 to become separated. Preferably, a cuffed intubation tube is used. When the leading edge of the tube is properly positioned the cuffed section of the tube is expanded to fixedly position the leading edge of the tube between the vocal cords and the branching of the main bronchi. The grasping and extending device can then be removed. If an uncuffed tube is used the grasping and extending device 27 and the tube can be separated by the operator simply holding the tube proximate the patients mouth and withdrawing the grasping and extending device 27 from the tube. The positioning of the tube can of course be checked and adjusted as known in the art. After placement of the tube 12, or at least the leading portion of the tube 12, the operator can then remove the laryngoscope from the patient. The present invention thus allows for a faster, more precise and individualized access to the larynx and trachea region of a patient and placement of the tube in the trachea.

Figure 8:
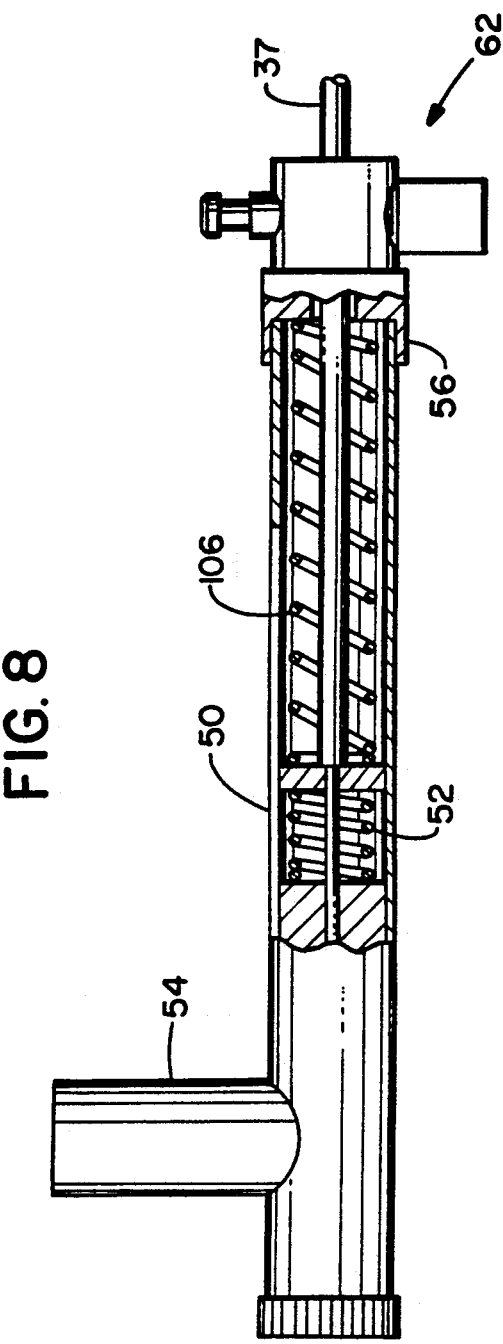
FIG. 8 is a diagrammatical partial cross-sectional view of the control for an alternative embodiment of the invention.

Referring now to FIG. 8, a diagrammatical cross-sectional view of an alternative embodiment of the control 34 is shown. In this embodiment, a second biasing spring 106 is provided in the slide tube 50 between the stop sleeve 58 and contact sleeve 56. In this embodiment, the second biasing spring 106 automatically biases the control 34 to position the grasping and extending device 27 in the first or home position. The first spring 52 is sufficiently stronger then the second spring 106 such that the jews 44 and 46 will not open prematurely. Alternatively, alternate means could be provided to prevent the jaws from opening until desired.

Alternate embodiments of the invention might include a laryngoscope having a relatively straight blade 14. Alternatively the present invention can be used with flexible laryngoscopes or the grasping and extending device 27 may be manufactured such that the distal end is controllably deflectable. The grasping and extending device 27 may be substantially rigid or a combination of partially rigid and partially flexible. Alternatively, the blade may be flexible. In addition, the present invention can be used for placement of objects other than intubation tubes or can be used for the removal or reorientation of objects.

It should be understood that the foregoing description is only illustrative of the invention. Various alternatives and modification can be devised by those skilled in the art without departing from the spirit of the invention. Accordingly, the present invention is intended to embrace all such alternatives, modifications and variances which fall within the scope of the appended claims.

What is claimed is:

1. A method of placing an object into the larynx and trachea region of a patient comprising the steps of:
    inserting a laryngoscope having a placement device movably connected therewith into the patient;
    conecting the object to the placement device; moving a distal portion of the placement device from a first home position proximate a distal region of the laryngoscope to a second extended position, the object to be placed also moving relative with the distal portion of the placement device; and
    releasing the object to be placed from the placement device.

2. A method as in claim 1 further comprising connecting said object to the placement device by placing closing movable grasping jaws onto the object.

3. A method as in claim 1 further comprising the step of controlling the movement of the placement device and the release of the object by means of a control means.

4. A method as in claim 1 further comprising the step of removing the laryngoscope from the patient.

5. A method of placing a tube into the larynx and trachea region of a patient comprising the steps of:
    providing a laryngoscope having a rigid frame, a working channel in the frame, and a movable placement device located in the working channel having a grasping device at a distal region thereof and being comnnected to the frame at a proximal region thereof;
    grasping a leading portion of the tube at the grasping device;
    inserting the laryngoscope frame into the patient with the leading portion of the tube being located at a first position proximate the distal region of the laryngoscope frame;
    moving the placement device relative to the laryngoscope frame and thereby extending the grasping device and leading portion of the tube to a second position extended from the distal region of the laryngoscope frame; and
    releasing the tube from the grasping device.

6. A method as in claim 5 further comprising the step of controlling the grasping and releasing of the tube by a control means.

* * * * *